(12) United States Patent
Kawashima

(10) Patent No.: US 7,494,400 B2
(45) Date of Patent: Feb. 24, 2009

(54) MANUFACTURING METHOD FOR A MULTILAYERED GAS SENSOR ELEMENT

(75) Inventor: Yukio Kawashima, Yokkaichi (JP)

(73) Assignee: Denso Corporation (JP)

( * ) Notice: Subject to any disclaimer, the term of this patent is extended or adjusted under 35 U.S.C. 154(b) by 872 days.

(21) Appl. No.: 10/778,203

(22) Filed: Feb. 17, 2004

(65) Prior Publication Data

US 2004/0158971 A1 Aug. 19, 2004

(30) Foreign Application Priority Data

Feb. 18, 2003 (JP) ............................. 2003-039846

(51) Int. Cl.
*G01N 27/407* (2006.01)
(52) U.S. Cl. ...................... 451/28; 204/424; 156/89.12; 73/1.06
(58) Field of Classification Search ................. 204/424, 204/427; 451/28; 156/89.12; 73/1.06
See application file for complete search history.

(56) References Cited

U.S. PATENT DOCUMENTS

| | | | |
|---|---|---|---|
| 5,144,249 A | 9/1992 | Kurishita et al. | |
| 5,357,716 A * | 10/1994 | Kishida et al. | 451/390 |
| 5,674,110 A * | 10/1997 | Cuoghi | 451/44 |
| 6,569,303 B1 | 5/2003 | Moriguchi et al. | |
| 6,645,360 B1 | 11/2003 | Eisele et al. | |
| 6,805,830 B1 | 10/2004 | Graser et al. | |

FOREIGN PATENT DOCUMENTS

| | | |
|---|---|---|
| JP | 64-71654 | 3/1989 |
| JP | 3-272448 | 12/1991 |
| JP | 10-104184 | 4/1998 |
| JP | 2000-511644 | 9/2000 |
| JP | 2001-66280 | 3/2001 |
| JP | 2001-153835 | 6/2001 |
| JP | 2002-340843 | 11/2002 |
| JP | 2003-502664 | 1/2003 |

OTHER PUBLICATIONS

Machine translation of JP 10-104,184, Apr. 1998.*
Machine translation of JP 2001-153835, Aug. 2001.*
JPO Search Report with translation dated Feb. 21, 2006.

* cited by examiner

*Primary Examiner*—Kaj K Olsen
(74) *Attorney, Agent, or Firm*—Nixon & Vanderhye PC

(57) ABSTRACT

In manufacturing a multilayered gas sensor element which includes a sensor cell for measuring a specific gas concentration in a measured gas, a main body portion including a plurality of laminated ceramic substrates, and a plate heater portion generating heat in response to supply of electric power, which are integrally laminated in a predetermined order, a multilayered body of green sheets forming the main body portion and the heater portion is sintered into a multilayered gas sensor element, and then at least both side surfaces of the multilayered gas sensor element extending in a longitudinal direction are processed by grinding, so as to remove surface defects.

8 Claims, 11 Drawing Sheets

MANUFACTURING METHOD FOR A MULTILAYERED GAS SENSOR ELEMENT

BACKGROUND OF THE INVENTION

The present invention relates to a manufacturing method for a multilayered gas sensor element to be incorporated in an exhaust gas system for an internal combustion engine to control the combustion of the engine.

Multilayered gas sensing elements are preferably installed in exhaust gas systems of automotive engines to measure various gas concentrations and control the combustion of the engines, and are arranged in the following manner.

For example, as disclosed in the Japanese Patent Application Laid-open No. 2001-66280, a conventional gas sensing element includes a solid electrolytic substance. A measured gas side electrode is provided on one surface of this solid electrolytic substance so as to be exposed to a measured gas. A porous diffusion resistance layer covers the outer surface of the measured gas side electrode. And, a dense protection layer covers the outer surface of the diffusion resistance layer. Furthermore, a reference electrode is provided on the other surface of the solid electrolytic substance so as to be exposed to a reference gas.

The above-described reference electrode is provided in a reference gas chamber into which the reference gas is introduced. The reference gas chamber is defined by laminating a spacer on the solid electrolytic substance. A heater portion is integrally laminated with the spacer. The heater portion consists of a heat generating element which generates heat in response to supply of electric power and a heater substrate provided with lead portions and terminal portions which are electrically connected to the heat generating element.

The multilayered gas sensor element, as described later in a preferred embodiment of the present invention, can be manufactured by sintering a laminated body of green sheets being appropriately laminated to constitute a diffusion resistance layer, a protection layer, a solid electrolytic substance, a spacer, and a heater substrate. However, as shown in FIG. 4, surface defects 195 such as chips and cracks tend to appear on side surfaces 193 and 194 and element surfaces 191 and 192 of a multilayered gas sensor element 1 as a result of sintering operation. Furthermore, there is the possibility that warpage appears on the side surfaces 191 and 192 of the multilayered gas sensor element 1 (refer to FIG. 4). Undesirable differences in altitudinal level may also be caused due to lamination error.

The above-described surface defects 195 may be not so large to give adverse influence to the operation of multilayered gas sensor element 1, for example, immediately after finishing the sintering operation. However, as shown in FIG. 5, this kind of surface defects 195 possibly grow into larger defects when electric power is supplied to a heater portion 18 and will stretch into the inner portion of the of the multilayered gas sensor element 1.

Accordingly, reducing such undesirable surface defects as much as possible is very important to improve the production yield in the manufacturing of the multilayered gas sensor elements.

SUMMARY OF THE INVENTION

In view of the above-described problems of the prior art, the present invention has an object to provide a manufacturing method for a multilayered gas sensor element which is capable of reducing the percentage of defective products having surface defects.

In order to accomplish the above and other related objects, the present invention provides a first method for manufacturing a multilayered gas sensor element which includes a sensor cell for measuring a specific gas concentration in a measured gas, a main body portion including a plurality of laminated ceramic substrates, and a plate heater portion generating heat in response to supply of electric power, which are integrally laminated in a predetermined order. The first manufacturing method of the present invention includes a step of sintering a multilayered body of green sheets forming the main body portion and the heater portion into a multilayered gas sensor element and a step of grinding at least both side surfaces of the multilayered gas sensor element extending in a longitudinal direction, thereby removing surface defects.

Furthermore, the present invention provides a second method for manufacturing a multilayered gas sensor element which includes a sensor cell for measuring a specific gas concentration in a measured gas, a main body portion including a plurality of laminated ceramic substrates, and a plate heater portion generating heat in response to supply of electric power, being integrally laminated in a predetermined order. The second manufacturing method of the present invention includes a step of sintering a multilayered body of green sheets forming the main body portion and the heater portion into a multilayered gas sensor element and a step of chamfering at least ridge portions of the multilayered gas sensor element existing between both side surfaces of the multilayered gas sensor element and an element surface adjacent to the heater portion along a longitudinal direction, thereby removing surface defects.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENT

Figure 1:
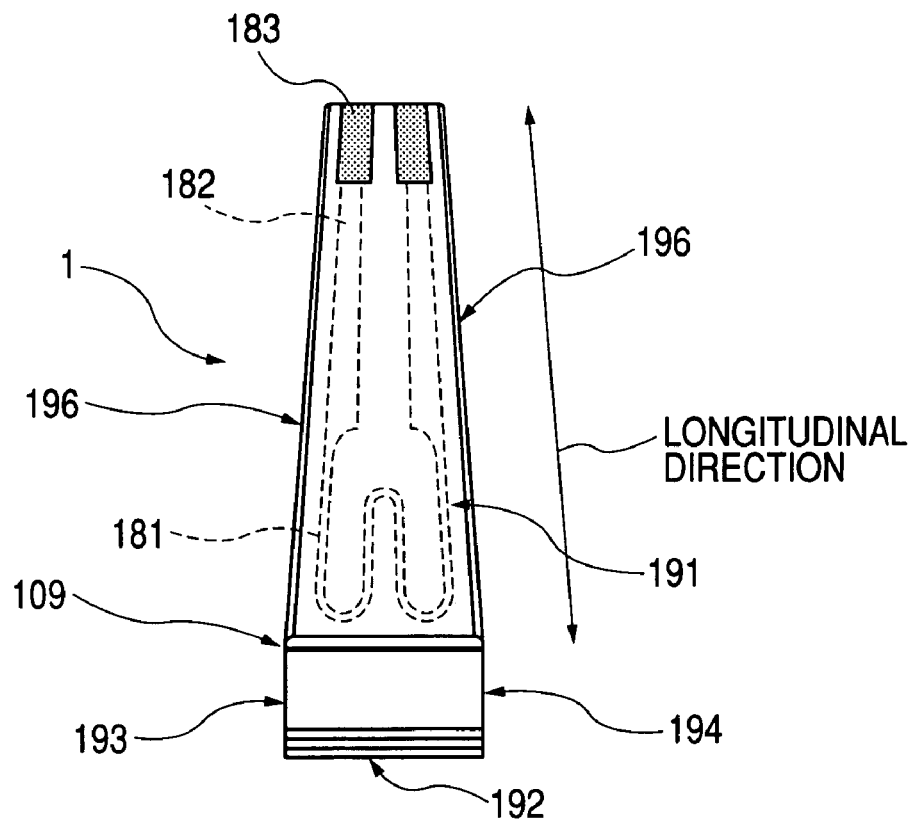
FIG. 1 is a perspective view showing a multilayered gas sensor element in accordance with a preferred embodiment of the present invention.

A preferred embodiment of the present invention will be explained hereinafter with reference to attached drawings.

Characteristic Features

The preferred embodiment of the present invention provides a first method for manufacturing a multilayered gas sensor element which includes a sensor cell for measuring a specific gas concentration in a measured gas, a main body portion including a plurality of laminated ceramic substrates, and a plate heater portion generating heat in response to supply of electric power, which are integrally laminated in a predetermined order. The first manufacturing method of the preferred embodiment includes a step of sintering a multilayered body of green sheets forming the main body portion and the heater portion into a multilayered gas sensor element, and a step of grinding at least both side surfaces of the multilayered gas sensor element extending in a longitudinal direction, thereby removing surface defects.

Furthermore, the preferred embodiment of the present invention provides a second method for manufacturing a multilayered gas sensor element which includes a sensor cell for measuring a specific gas concentration in a measured gas, a main body portion including a plurality of laminated ceramic substrates, and a plate heater portion generating heat in response to supply of electric power, being integrally laminated in a predetermined order. The second manufacturing method of the preferred embodiment includes a step of sintering a multilayered body of green sheets forming the main body portion and the heater portion into a multilayered gas sensor element, and a step of chamfering at least ridge portions of the multilayered gas sensor element existing between both side surfaces of the multilayered gas sensor element and an element surface adjacent to the heater portion along a longitudinal direction, thereby removing surface defects.

The functions and effects of the preferred embodiment will be explained hereinafter. In the process of manufacturing the multilayered gas sensor element, there is the possibility that small surface defects, such as chips and cracks, of 0.03 mm to 0.05 mm in largeness may appear. The surface defects will not give adverse effects to operations, functions, and performances of the multilayered gas sensor element if they are small in size and total number.

However, when the heater portion integrally formed as part of the multilayered gas sensor element generates heat in response to supply of electric power, the surface defects located adjacent to the heater portion grow into larger chips or cracks due to influence of thermal stress. The surface defects, if once grew large, give adverse effects to operations, functions, and performance of the multilayered gas sensor element. Furthermore, the surface defects may stretch into the inner portion of the element. Moreover, thermal stress possibly produces new surface defects.

The first or second manufacturing method of the preferred embodiment is characterized in the step of grinding at least both side surfaces of the multilayered gas sensor element or chamfering the ridge portions of the multilayered gas sensor element existing between both side surfaces of the multilayered gas sensor element and the element surface adjacent to the heater portion. In other words, the grinding operation is intensively and selectively applied to a specific region where the heater portion is adjacently located and accordingly the surface defects tend to grow due to heat generation. Thus, it becomes possible to remove the surface defects existing in the vicinity of the heater portion and accordingly becomes possible to reduce the total number of defective products of the multilayered gas sensor element resulting from the growth of this kind of surface defects. Especially, the first manufacturing method according to the preferred embodiment includes the step of grinding both side surfaces of the multilayered gas sensor element and accordingly brings the effects of unifying the shape of the sensor element and improving the assembling accuracy.

As described above, the preferred embodiment of the present invention can provide an excellent method for manufacturing a multilayered gas sensor element having less surface defects.

Preferable Arrangement

The side surface of the multilayered gas sensor element in accordance with the first or second manufacturing method of the preferred embodiment is a surface of the multilayered gas sensor element extending in the longitudinal direction perpendicularly to the lamination direction of the multilayered gas sensor element. The element surface adjacent to the heater portion is a surface perpendicular to the side surface and adjacent to the heater portion. It is preferable to apply the chamfering and grinding to other surfaces or ridge portions of the multilayered gas sensor element.

The multilayered gas sensor element according to the first or second manufacturing method of the preferred embodiment is, for example, a single-cell type oxygen sensor element detecting the oxygen concentration (i.e., a limiting-current type, or an oxygen concentration cell type), or an air-fuel ratio sensor element or a λ sensor element detecting a theoretical air-fuel ratio (i.e., λ point), or a two-cell type NOx sensor element, CO sensor element, HC sensor element, or the like, which are generally installed in an exhaust gas system of an internal combustion engine for an automotive engine or the like to measure an oxygen or unburnt gas concentration in the exhaust gas to detect the air-fuel ratio.

Furthermore, according to the first or second manufacturing method of the preferred embodiment, it is preferable to chamfer the ridge portions of the multilayered gas sensor element after grinding both side surfaces of the multilayered gas sensor element. Grinding the both side surfaces makes it possible to accurately form the side surfaces in parallel with each other. Accordingly, accuracy in positioning the sensor element in chamfering the ridge portions can be increased. Grinding the ridge portions becomes easy.

Furthermore, according to the first manufacturing method of the preferred embodiment, a preferable grinding depth of respective side surfaces is in the range from 0.1 mm to 0.2 mm. If the grinding depth is less than 0.1 mm, it will be difficult to sufficiently remove the surface defects. If the grinding depth is larger than 0.2 mm, a great amount of material corresponding to the grinding depth will be wasted and accordingly the manufacturing cost will increase. Furthermore, when the grinding depth is larger than 0.2 mm, there will be the possibility that the heat generating element (refer to a portion indicated by the reference numeral 181 in FIG. 1) or other inside component of the multilayered gas sensor element will be bared and damaged.

The grinding depth of respective side surfaces is a maximum distance between an original side surface position of the sensor element being not subjected to the grinding operation and a new side surface position of the sensor element resulting from the grinding operation. The maximum distance is a value measured in the width direction perpendicular to the longitudinal direction, as indicated by d1 in the later-described FIG. 2 or FIG. 10.

Furthermore, according to the second manufacturing method of the preferred embodiment, a preferable chamfering depth of the ridge portions is in the range from 0.05 mm to 0.35 mm. If the chamfering depth is less than 0.05 mm, it will be difficult to sufficiently chamfer the ridge portions to relax the stress induced from the thermal stress of the heater portion and accordingly becomes difficult to sufficiently suppress the growth of surface defects.

If the chamfering depth is larger than 0.35 mm, a great amount of material corresponding to the chamfering depth will be wasted and accordingly the manufacturing cost will increase. Furthermore, there will be the possibility that the heat generating element (refer to a portion indicated by the reference numeral 181 in FIG. 1) or other inside component of the multilayered gas sensor element will be bared and damaged.

The chamfering depth of respective ridge portions is a maximum distance between an original side surface position of the sensor element being not subjected to the chamfering operation and an edge position of a chamfered element surface adjacent to the heater portion. The maximum distance is a value measured in the width direction perpendicular to the longitudinal direction, as indicated by d2 in the later-described FIG. 2.

Furthermore, according to the first manufacturing method of the preferred embodiment, it is preferable that two side surface grinding disk grindstones, each rotating about its disk center, are disposed in parallel with each other to grind both side surfaces of the multilayered gas sensor element extending in the longitudinal direction, and the multilayered gas sensor element is introduced into a clearance between two side surface grinding disk grindstones to grind respective side surfaces thereof. With this arrangement, it becomes possible to simultaneously grind both of the side surfaces, thereby shortening the grinding time and improving the efficiency of the grinding operation.

Furthermore, it is preferable to inject grinding fluid (such as pure water) between two side surface grinding disk grindstones so that the grinding fluid can settle between these side surface grinding disk grindstones during the operation for grinding the side surfaces of the multilayered gas sensor element. This makes it possible to suppress the consumption of the grinding fluid and reduce the manufacturing cost. To sufficiently maintain the grinding fluid, it is preferable to provide a grinding fluid storage pocket on the confronting surfaces of the side surface grinding disk grindstones (refer to FIG. 13).

Furthermore, according to the first manufacturing method of the preferred embodiment, it is preferable that the multilayered gas sensor element is substantially supported and fixed at point when the multilayered gas sensor element is introduced into the clearance between two side surface grinding disk grindstones to grind the side surfaces of the multilayered gas sensor element.

If the multilayered gas sensor element having any warpage or bending is introduced into the clearance between two side surface grinding disk grindstones to grind the side surfaces of the multilayered gas sensor element, a large force may act on the multilayered gas sensor element and will possibly break the element body. Therefore, to allow the multilayered gas sensor element to move freely to a certain degree, the multilayered gas sensor element is supported at point. Especially, supporting the multilayered gas sensor element at point allows the multilayered gas sensor element to move in the width direction perpendicular to the longitudinal direction. A sufficient degree of freedom is kept in the movement of the multilayered gas sensor element when the multilayered gas sensor element is introduced into the clearance between two side surface grinding disk grindstones. Thus, no large force acts on the multilayered gas sensor element. The element body will not be broken.

Furthermore, according to the first manufacturing method of the preferred embodiment, it is preferable that a holder is used to support and fix the multilayered gas sensor element when the multilayered gas sensor element is introduced into the clearance between two side surface grinding disk grindstones to grind the side surfaces of the multilayered gas sensor element, and a portion of the holder being directly brought into contact with the multilayered gas sensor element is made of an elastic member.

With this arrangement, it becomes possible to prevent the holder from damaging the surface of the multilayered gas sensor element. Furthermore, it becomes possible to assure a degree of freedom in the movement of the gas sensor element during the grinding operation of the side surfaces of the gas sensor element. The above-described elastic member is, for example, a resin, a rubber, or a urethane rubber.

Figure 7:
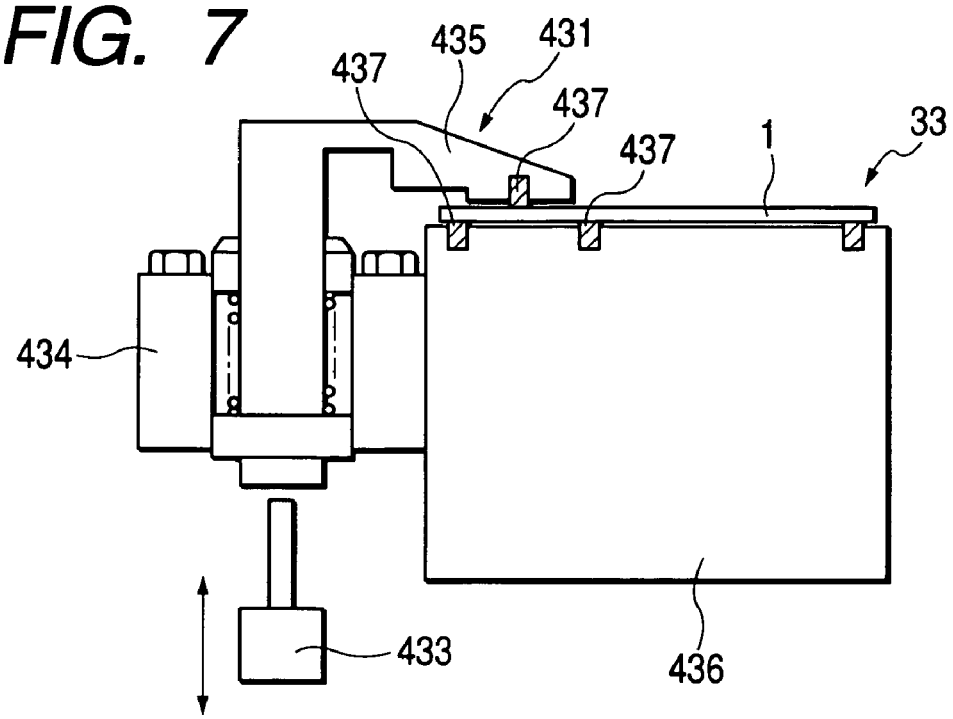
FIG. 7 is a view showing a side surface grinding section of the grinding apparatus in accordance with the preferred embodiment of the present invention.

Furthermore, it is preferable that the above-described elastic member is configured into a columnar shape as shown in FIG. 7. This shape is advantageous in low manufacturing cost. A circular portion of the columnar elastic member is asymmetric and has no directivity, and accordingly can contact with the multilayered gas sensor element without causing any undesirable or excessive force acting on the element body.

Furthermore, according to the first manufacturing method of the preferred embodiment, it is preferable that the multilayered gas sensor element is introduced into the clearance between two side surface grinding disk grindstones to grind the side surfaces of the multilayered gas sensor element, being led from a longitudinal front end side where the sensor cell is present.

In general, as explained in the first embodiment of the preferred embodiment, the multilayered gas sensor element equipped with a sensor cell has a diffusion resistance layer or a dense protection layer covering an electrode constituting the sensor cell. Accordingly, the front end side of the sensor element where the sensor cell is provided is thick and has a higher mechanical strength due to the presence of the diffusion resistance layer or the dense protection layer. Introducing the multilayered gas sensor element from the direction having a higher mechanical strength is effective in preventing the element body from being broken by a pressing force or a shock.

Figure 6:
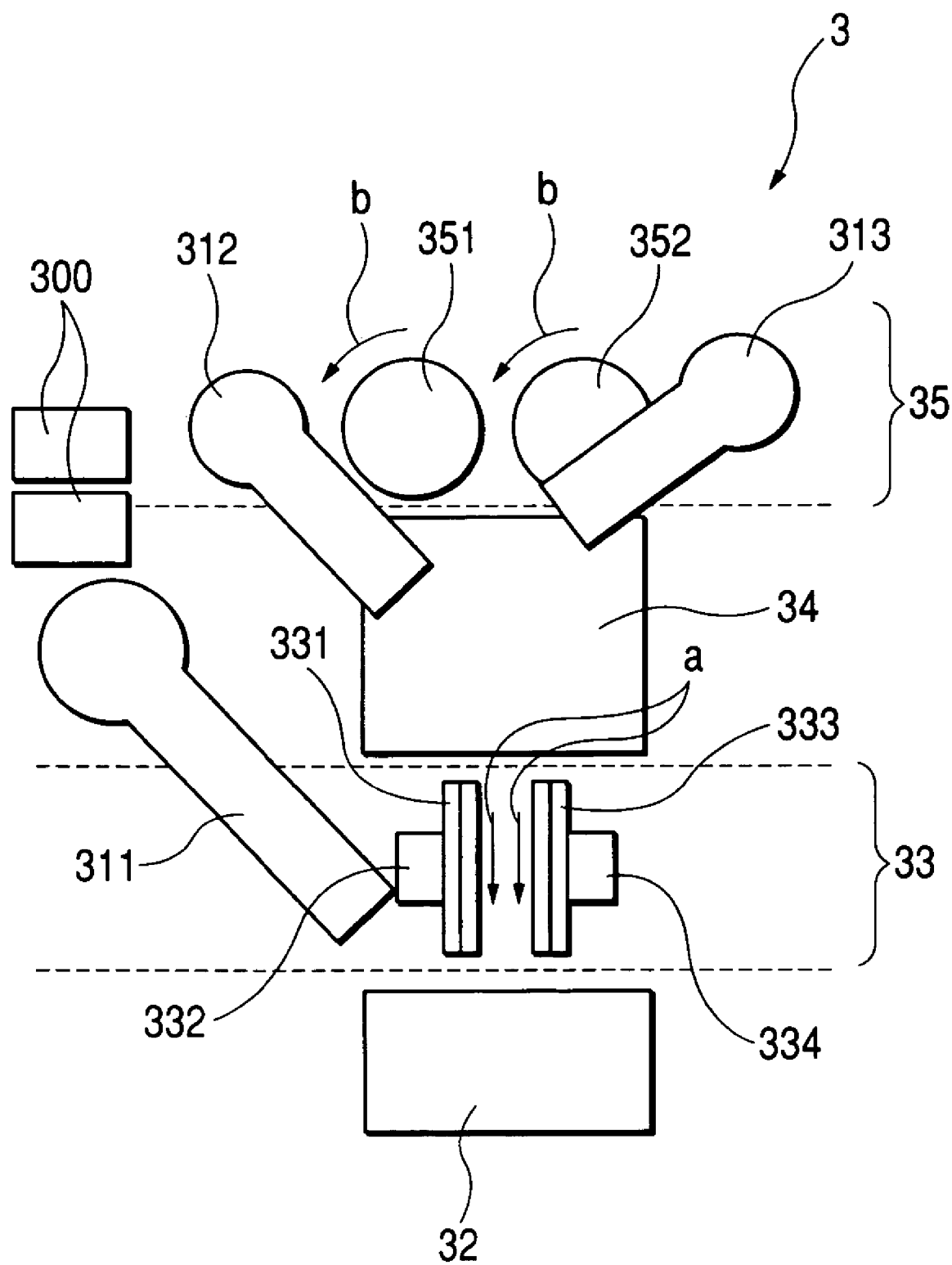
FIG. 6 is a view showing a grinding apparatus in accordance with the preferred embodiment of the present invention.

Furthermore, according to the second manufacturing method of the preferred embodiment, it is preferable that a ridge chamfering disk grindstone rotating about its disk center is prepared to chamfer the ridge portions of the multilayered gas sensor element, and the ridge portions of the multilayered gas sensor element are chamfered by pressing respective ridge portions against a disk surface of the ridge chamfering disk grindstone. With this arrangement, respective ridge portions can be efficiently chamfered. Furthermore, it is possible to provide a pair of ridge chamfering disk grindstones adjacently to simultaneously chamfer the ridge portions of two multilayered gas sensor elements as shown in FIG. 6.

Furthermore, according to the second manufacturing method of the preferred embodiment, it is preferable that the longitudinal direction of the multilayered gas sensor element is located in parallel with a rotational direction of the ridge chamfering disk grindstone when the respective ridge portions of the multilayered gas sensor element are pressed against the disk surface of the ridge chamfering disk grindstone.

If the pressing direction is not in the above-described parallel relationship, it will be difficult to suppress generation of chipping. This will lead to production of defective sensor elements. On the contrary, according to the above-described arrangement of the preferred embodiment, the longitudinal direction of the multilayered gas sensor element is parallel to the rotational direction of the ridge chamfering disk grindstone. Thus, it becomes possible to suppress generation of chipping. The chipping generally represents surface defects of the sensor element appearing in the direction vertical to the element longitudinal direction. Especially, the surface defects having the size exceeding 0.03 mm tend to grow into larger defects giving adverse influence to operations, functions, and performances of the multilayered gas sensor element when electric power is supplied to the heater portion.

Furthermore, according to the second manufacturing method of the preferred embodiment, it is preferable that the ridge portions of the multilayered gas sensor element are chamfered by changing a position where the ridge portions of the multilayered gas sensor element are pressed against the ridge chamfering disk grindstone.

Hereinafter, the reasons why the chamfering operation is performed by changing the pressing position will be explained. This chamfering operation includes a first step of pressing a ridge portion against the ridge chamfering disk grindstone at an arbitrary position in the beginning of this chamfer operation, a second step of once releasing the ridge portion from the ridge chamfering disk grindstone, and a third step of pressing the ridge portion against the ridge chamfering disk grindstone at a position different from the initially selected position.

Regarding the methods for rotating a disk grindstone, there are mainly classified into a constant rotational speed type (i.e., a constant angular speed type) and a constant circumferential speed type (i.e., a constant line speed type). The constant rotational speed type is advantageous in that the structure of a motor used for rotating the disk grindstone can be simplified. However, the pressing time of the ridge portion needs to be changed depending on the position where the ridge portion is pressed against the disk grindstone (namely, depending on the distance from the disk center of the disk grindstone).

To chamfer the same amount, the pressing time needs to be enlarged when the ridge portion is pressed against the radial inner side of the disk grindstone (i.e., a position close to the disk center) while needs to be reduced when pressed against the radial outer side of the disk grindstone (i.e., a position far from the disk center). This is because, according to the constant angular speed type, the circumferential speed of the disk grindstone is slow at the inner circumferential portion and fast at the outer circumferential portion.

In general, from the view point of manufacturing process management and work efficiency, it is desirable that the time required for accomplishing the grinding operation for the ridge portion of each multilayered gas sensor element is constant. Accordingly, there is the tendency that the grinding operation for all of the multilayered gas sensor elements is performed by using the same position of the disk grindstone (i.e., at the constant distance from the disk center). However, in this case, the disk grindstone is locally worn out and accordingly the lifetime of the disk grindstone will be shortened. To eliminate this drawback, instead of performing the ridge grinding operation by continuously pressing the multilayered gas sensor element against the same position of the disk grindstone, it is preferable to repetitively perform the ridge grinding operation by changing the position where the multilayered gas sensor element is pressed against the disk grindstone within a constant time allocated for accomplishing the ridge grinding operation of each multilayered gas sensor element. According to this method, the grinding operation of each the multilayered gas sensor element is carried out by using a plurality of different positions of the disk grindstone (i.e., positions different in the distance from the disk center).

This makes it possible to accomplish the ridge chamfering operation for each multilayered gas sensor element within a constant time. The processing cycle in the manufacturing of the multilayered gas sensor element becomes constant and stable. Furthermore, it becomes possible to prevent the ridge chamfering disk grindstone from being locally worn out and accordingly the lifetime of the grindstone can be extended.

Furthermore, according to the second manufacturing, method of the preferred embodiment, it is preferable that the ridge portions of the multilayered gas sensor element are pressed against the ridge chamfering disk grindstone for a relatively long time when the ridge portions are brought into contact with an inner circumferential portion of the ridge chamfering disk grindstone adjacent to its disk center, and are pressed for a relatively short time when the ridge portions are brought into contact with an outer circumferential portion of the ridge chamfering disk grindstone far from its disk center, when the ridge portions of the multilayered gas sensor element are chamfered.

Namely, the pressing time is changed in accordance with the position where the multilayered gas sensor element is pressed against the ridge chamfering disk grindstone in the ridge chamfering operation, in such a manner that the pressing time becomes long when the multilayered gas sensor element is pressed against the inner circumferential portion of the ridge chamfering disk grindstone and becomes short when pressed against outer circumferential portion. With this setting, it becomes possible to uses the ridge chamfering disk grindstone as a constant rotational speed type (i.e., a constant angular speed type). The structure of a motor used for rotating the ridge chamfering disk grindstone can be simplified.

Furthermore, according to the second manufacturing method of the preferred embodiment, it is preferable that an angular velocity of the ridge chamfering disk grindstone is high at the inner circumferential portion adjacent to the disk center and low at the outer circumferential portion far from the disk center, when the ridge portions of the multilayered gas sensor element are chamfered. Increasing the angular velocity of the inner circumferential portion to a higher speed and decreasing the angular velocity of the outer circumferential portion to a lower speed makes it possible to use the ridge chamfering disk grindstone as a constant circumferential speed type (i.e., a constant line speed type). To realize the above-described rotation, a variable (inverter) motor will be necessary. The same amount of chamfering is feasible during the same period of time regardless of the position where the multilayered gas sensor element is pressed against the ridge chamfering disk grindstone. This prevents the ridge chamfering disk grindstone from being locally worn and substantially extends the lifetime of the grindstone. The processing time required for chamfering the ridge portions of each multilayered gas sensor element can be unified. The processing cycle in the manufacturing of the multilayered gas sensor element becomes constant and stable.

Furthermore, according to the second manufacturing method of the preferred embodiment, it is preferable that the multilayered gas sensor element is swung in the longitudinal direction when the ridge portions of the multilayered gas sensor element are pressed against the ridge chamfering disk grindstone to chamfer the ridge portions. This is effective to perform the ridge chamfering operation stably in a case that the multilayered gas sensor element has a warped surface.

Furthermore, according to the second manufacturing method of the preferred embodiment, it is preferable that the multilayered gas sensor element is reversed in the longitudinal direction after one of the ridge portions of the multilayered gas sensor element is pressed against the ridge chamfering disk grindstone to chamfer this ridge portion, and the other of the ridge portions is pressed against the ridge chamfering disk grindstone to chamfer this other ridge portion. Although each sensor element has two ridge portions to be chamfered, the chamfering operation for each sensor element can be done without re-holding the sensor element. The manufacturing process can be simplified.

Furthermore, according to the first or second manufacturing method of the preferred embodiment, it is preferable that after removing the surface defects from the sensor element the discrimination between a detective product and a non-defective product is carried out by inspecting the processed surfaces obtained by grinding both side surfaces or obtained by chamfering the ridge portions with an image recognizing apparatus to check whether or not these surfaces satisfy predetermined size requirements, inspecting the presence of any chipping caused in the grinding or chamfering operation, visually inspecting the presence of any growth of surface defects by supplying electric power to the heater portion, and inspecting the largeness of an insulation resistance of the multilayered gas sensor element.

Through the above-described inspections, non-defective multilayered gas sensor elements can be surely obtained. Accordingly, it becomes possible to provide an excellent manufacturing method for a multilayered gas sensor element which can assure good value in production yield.

Overall Arrangement

Hereinafter, a practical arrangement of the preferred embodiment will be explained with reference to the attached drawings.

As shown in FIGS. 1 to 5, a multilayered gas sensor element 1 includes a sensor cell 100 which measures a specific gas concentration in a measured gas, a main body portion 10 which consists of a plurality of ceramic substrates being laminated, and a plate heater portion 18 generating heat in response to supply of electric power, which are integrally laminated in a predetermined order.

The multilayered gas sensor element 1 is manufactured in the following manner.

Green sheets for forming the main body portion 10 and a green sheet for forming the heater portion 18 are integrated into a laminated body. Then, the laminated body is sintered to obtain the multilayered gas sensor element 1. Then, surface defects 195 are removed of the multilayered gas sensor element 1 by grinding both side surfaces 193 and 194 extending in the longitudinal direction and also by chamfering and grinding ridge portions 196 formed between respective side surfaces 193 and 194 and an element surface 191 adjacent to the heater portion 18.

More specifically, the multilayered gas sensor element 1 is a limiting-current type sensor element capable of measuring an oxygen concentration in a measured gas.

Figure 3:
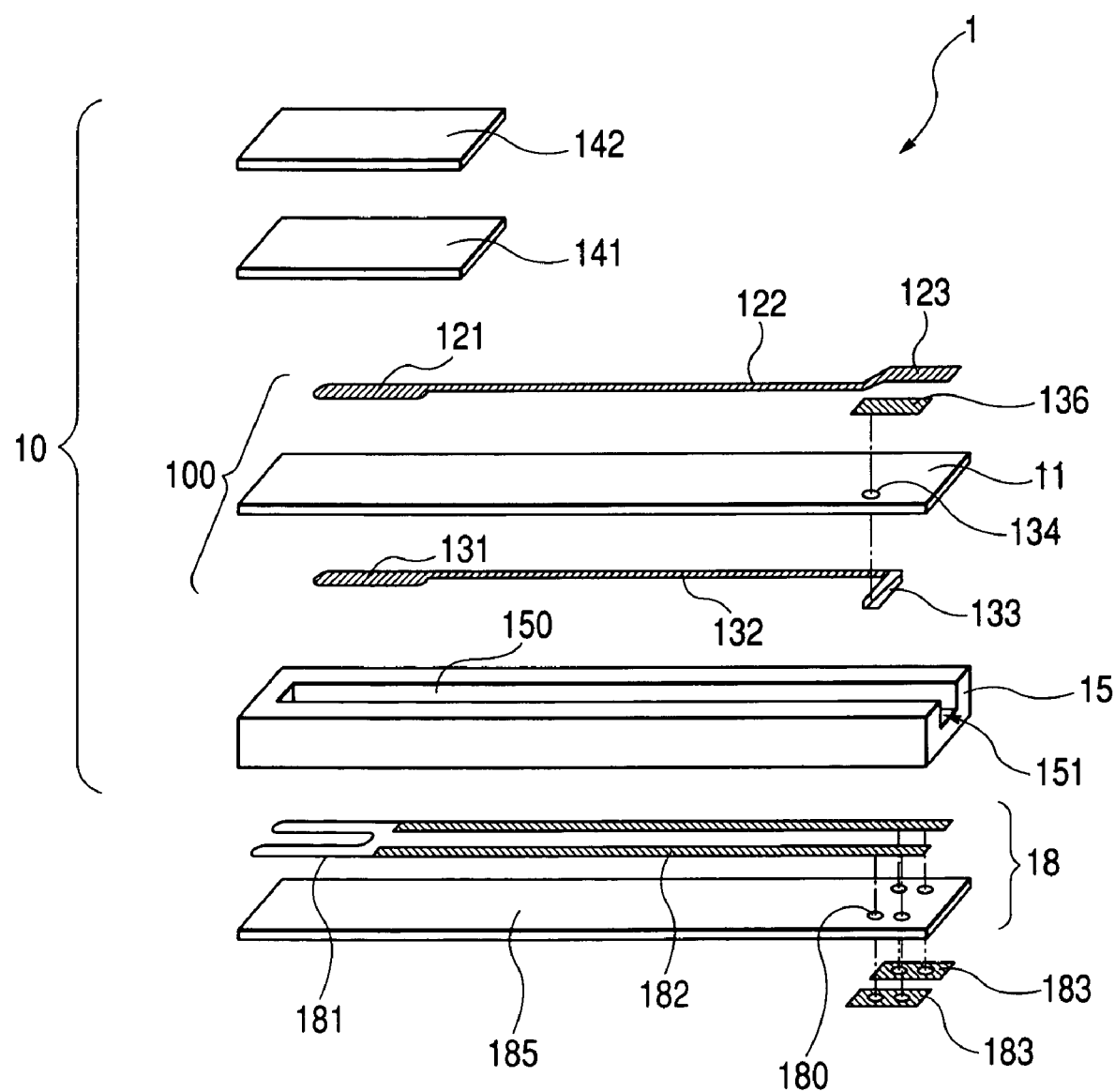
FIG. 3 is an exploded perspective view showing the multilayered gas sensor element in accordance with the preferred embodiment of the present invention.

As shown in FIGS. 1 and 3, the multilayered gas sensor element 1 includes a solid electrolytic substance 11, a reference gas chamber forming spacer 15, and the heater portion 18 which are laminated in a predetermined order. The solid electrolytic substance 11 has one surface on which a measured gas side electrode 121, a lead portion 122 and an external terminal 123 are provided. The lead portion 122 and the external terminal 123 are electrically conductive with the measured gas side electrode 121.

The measured gas side electrode 121 is covered with a diffusion resistance layer 141 which is porous and gas-permeable. The diffusion resistance layer 141 is covered with a dense protection layer 142 which is not gas-permeable. In FIG. 1, a reference numeral 109 represents a front end portion of the sensor body in the longitudinal direction where the sensor cell 100 is provided.

The solid electrolytic substance 11 has the other surface on which a reference electrode 131, a lead portion 132, and an internal terminal 133 are provided. The lead portion 132 and the internal terminal 133 are electrically conductive with the reference electrode 131. The internal terminal 133 is connected via a through-hole 134 to a reference side external terminal 136 located next to the external terminal 123. The reference electrode 131 is located in a reference gas chamber 150 defined by the spacer 15 so as to be exposed to a reference gas. The above-described spacer 15 is configured into a rectangular thick plate with a groove extending in the longitudinal direction. This groove substantially defines the reference gas chamber 150 when the spacer 15 is assembled with the solid electrolytic substance 11. The reference gas chamber 150 is isolated from a measured gas environment. The reference gas chamber 150 has an opening 151 through which air is introduced into the reference gas chamber 150. If the external gas around the sensor element is erroneously introduced into the reference gas chamber 150, the multilayered gas sensor element 1 cannot accurately measure the oxygen concentration.

The above-described heater portion 18 includes a heater substrate 185 on which a heat generating element 181, heater lead portions 182, and heater terminals 183 are provided. The heat generating element 181 generates heat in response to supply of electric power. The heater lead portions 182 are electrically conductive with the heat generating element 181. The heater terminals 183 are provided on an outer surface of the heater substrate 185 (i.e., the outer surface of the multilayered gas sensor element 1) which is opposed to the inner surface of the heater substrate 185 on which the heat generating element 181 is provided. The heater terminals 183 are connected to the heater lead portions 182 via through-holes 180 which extend vertically across the heater substrate 185.

The multilayered gas sensor element 1 is manufactured in the following manner.

First, a zirconia green sheet to be processed into the solid electrolytic substance 11 is manufactured from a paste containing zirconia powder including alumina powder and a stabilizing agent such as yttria. Then, by using a platinum paste, a plurality of printed portions to be processed into the electrodes 121 and 131, the lead portions 122 and 132, the external terminals 123 and 136, and the internal terminal 133 are provided on the surface of the above-described zirconia green sheet.

A molded body to be processed into the spacer 15 with a groove serving as the reference gas chamber 150 is manufactured from an alumina paste containing alumina powder by injection molding. Furthermore, an alumina green sheet to be processed into the heater substrate 185 is manufactured from the above-described alumina paste. Then, by using a platinum paste, a plurality of printed portions to be processed into the heat generating element 181, the lead portions 182, and the heater terminals 183 are provided on the surface of the above-described alumina green sheet. Furthermore, smaller alumina green sheets to be processed into the diffusion resistance layer 141 and the dense protection layer 142 are prepared.

Figure 4:
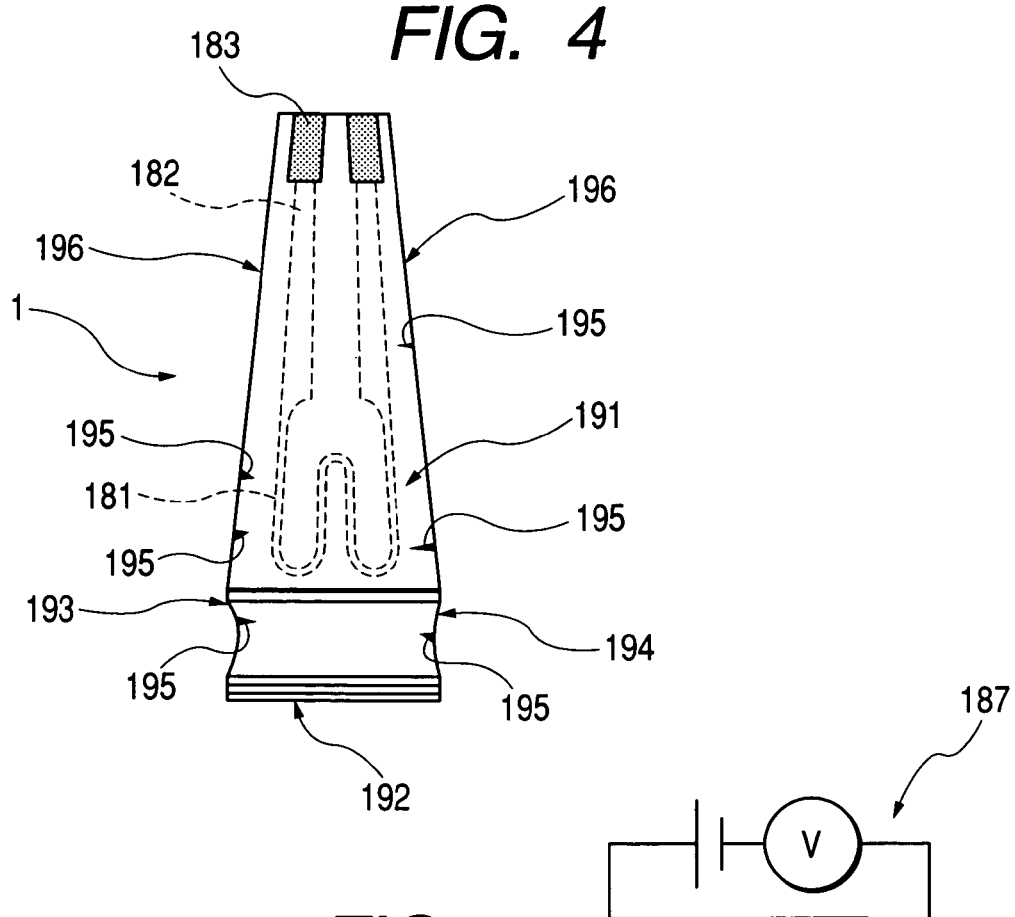
FIG. 4 is a perspective view showing surface defects having appeared on the multilayered gas sensor element as a result of a sintering operation.

The green sheets being thus prepared beforehand are laminated together in a predetermined order as shown in FIG. 3 and pressed to form a laminated body. The laminated body is sintered to obtain the multilayered gas sensor element 1. The multilayered gas sensor element 1, immediately after accomplishing the sintering operation, has various surface defects 195 as shown in FIG. 4. Furthermore, warpage directed inward is caused on the side surfaces 193 and 194. In this case, the surface defects 195 include micro cracks, chips, crazes, and breaks whose size is approximately 0.03 mm or less.

As shown in FIG. 1, the multilayered gas sensor element 1 has a rectangular solid shape. FIG. 1 is a perspective view showing the element surface 191 adjacent to the heater portion 18 facing upward, in which reference numerals 193 and 194 represent the side surfaces of the multilayered gas sensor element 1 extending in the longitudinal direction and reference numeral 192 represents an element surface adjacent to the main body portion 10 of the multilayered gas sensor element 1.

Figure 2:
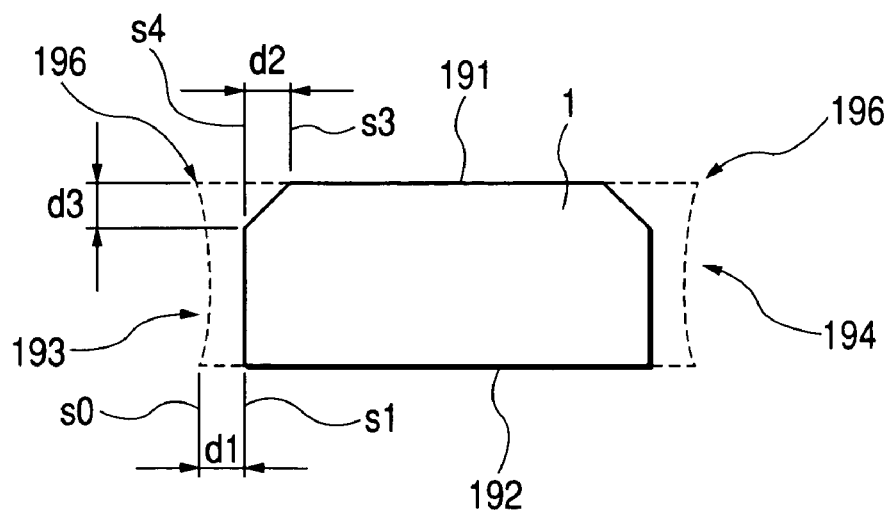
FIG. 2 is a cross-sectional view showing the multilayered gas sensor element in accordance with the preferred embodiment of the present invention.

FIG. 2 is a cross-sectional view showing a cross section of the multilayered gas sensor element 1, taken along a plane transversal to the side surfaces 193 and 194 and extending in the lamination direction. In FIG. 2, a dotted line represents the contour of the sensor element in a condition before executing the grinding operation and a solid line represents the contour of the sensor element in a condition after finishing the grinding operation. In this manner, by chamfering and grinding the ridge portions 196 formed between respective side surfaces 193 and 194 and the element surface 191 and also grinding the side surfaces 193 and 194, the side surfaces are finished to be substantially parallel to each other. Regarding the order of grinding operations, the grinding of side surfaces 193 and 194 is first performed and the chamfering and grinding of ridge portions 196 is performed subsequently. Furthermore, the grinding depth d1 of the side surface 193 is set to be 0.15 mm. The grinding depth d2 of the ridge portion 196 existing between the side surface 193 and the element surface 191 is set to be 0.2 mm. The remaining dimension d3 is set to be 0.2 mm.

The grinding depth d1 of respective side surfaces 193 and 194 is a maximum distance between an original side surface position s0 of the sensor element being not subjected to the grinding operation and a new side surface position s1 of the sensor element resulting from the grinding operation. The maximum distance is a value measured in the width direction perpendicular to the longitudinal direction. Furthermore, according to this embodiment, grinding operation of the ridge portions 196 is performed after grinding the side surfaces 193 and 194. Through these grinding operations, the both side surfaces 193 and 194 of the multilayered gas sensor element can be surely finished to be parallel to each other. Positioning the sensor element for the chamfering operation of ridge portions 196 can be realized with high accuracy. The grinding operation for the ridge portions 196 becomes easy.

The grinding depth d2 of the ridge portion 196 is a maximum distance between an original side surface position s4 of the sensor element being not subjected to the grinding operation and a new edge position s3 of the element surface 191 adjacent to the heater portion and resulting from the grinding operation. The maximum distance is a value measured in the width direction perpendicular to the longitudinal direction. According to this embodiment, the grinding operation of side surfaces 193 and 194 precedes the grinding operation of ridge portions 196. Thus, the side surface positions s1 and s4 are identical with each other (i.e., s1=s4).

With respect to the multilayered gas sensor elements being subjected to the above-described grinding operations according to the preferred embodiment of this invention, the rate of defective products was measured in the following manner.

Figure 5:
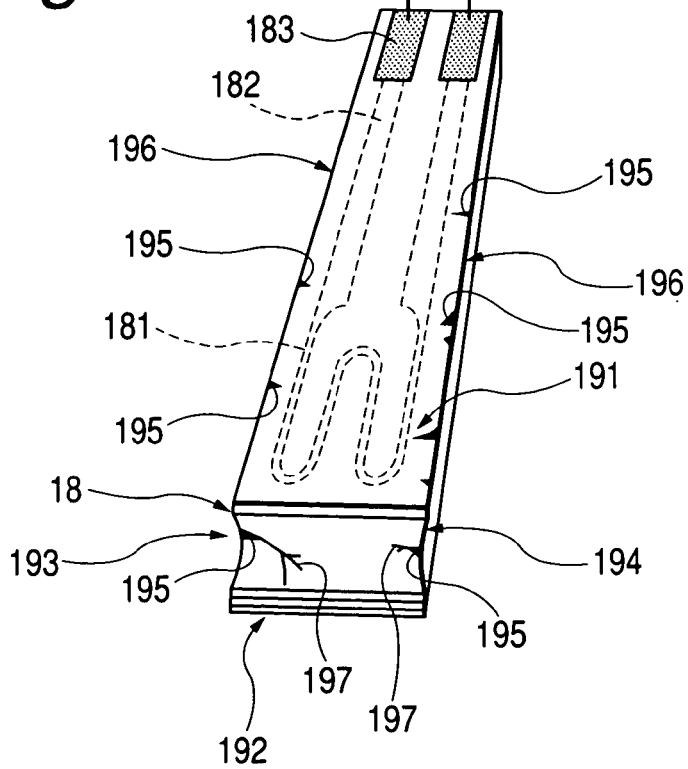
FIG. 5 is a perspective view showing the growth of surface defects of the multilayered gas sensor element due to heat generation caused by the heater portion in response to supply of electric power.

After finishing the manufacturing of the multilayered gas sensor element 1 shown in FIGS. 1 to 3 according to the above-described method, both of the side surfaces 193 and 194 and the ridge portions 196 were processed (i.e., ground) with a later-described grinding apparatus. Thereafter, as shown in FIG. 5, an electric power source circuit 187 including an electric power source and a voltmeter supplied electric voltage of 14.5 V to the heater portion 18 via the heater terminal portion 183 and the heater lead portion 182 for one minute, to cause the heater portion 18 to generate heat. After stopping the supply of electric power, the surfaces of the multilayered gas sensor element 1 were observed. However, no growth of cracks, chips, crazes, and breaks was confirmed.

Meanwhile, a comparable multilayered gas sensor element being manufactured under the same conditions and subjected to no grinding operation was prepared. Then, under the same conditions, electric power was supplied to the heater portion of this comparable sensor element. As a result, transverse cracks were observed in the width direction of the element surface adjacent to the heater portion.

Next, the performance of a sensor element being processed by grinding and the performance of a sensor element being not processed by grinding were evaluated based on a measured resistance value of the heat generating element of the heater portion. As a result, it was confirmed that the multilayered gas sensor element being processed by grinding has a predetermined resistance value while the sensor element being not processed by grinding has an infinite resistance value. Namely, breakage of a heat generating element has occurred in the sensor element being not processed by grinding.

Hereinafter, functions and effects of the above-described embodiment will be explained.

The heater portion 18, being integrally laminated in the multilayered gas sensor element 1, generates heat in response to supply of electric power. In this case, the surface defects 195 located adjacent to the heater portion 18 grow due to influence of the thermal stress and become so large that adverse influence is given to operations, functions, and performances of the multilayered gas sensor element 1. Furthermore, the surface defects 195 may grow into larger defects stretching into the inner portion of the sensor element (as indicated by reference numeral 197 in FIG. 5). Furthermore, as shown in FIGS. 4 and 5, the total number of the surface defects 195 possibly increases.

The manufacturing method of the above-described preferred embodiment is characterized in the step of grinding at least both side surfaces 193 and 194 of the multilayered gas sensor element 1 or chamfering and grinding the ridge portions 196 of the multilayered gas sensor element 1 formed between respective side surfaces 193 and 194 and the element surface 191 adjacent to the heater portion 18.

In other words, the grinding operation is intensively and selectively applied to a specific region where the heater portion 18 is adjacently located and accordingly the surface defects 195 tend to grow due to heat generation. Thus, it becomes possible to reduce the total number of surface defects 195 existing in the vicinity of the heater portion 18 and accordingly becomes possible to reduce the total number of defective products of the multilayered gas sensor element 1 resulting from the growth of this kind of surface defects 195.

Furthermore, even if some surface defects 195 exist initially on the element body, it is possible to remove these defects by a certain degree of grinding. Thus, even when new surface defects appear due to heat generation of the heater portion 18, the multilayered gas sensor element 1 manufactured according to the above-described preferred embodiment will have a small number or amount of surface defects compared with a conventional sensor element. According to the above-described preferred embodiment, the ridge portions 196 are processed by chamfering and grinding. This is effective to relax a stress caused by the thermal stress of heater portion 18 and prevent the surface defects 195 from growing.

As described above, the above-described preferred embodiment can provide an excellent method for manufacturing a multilayered gas sensor element having less surface defects.

Grinding Apparatus

FIG. 6 shows a grinding apparatus 3 performing the above-described grinding operation of the preferred embodiment of the present invention. As shown in FIG. 6, the grinding apparatus 3 has a loader section 32, a side surface grinding section 33, an unloader section 34, a ridge chamfering section 35, and a plurality of robot arms 311 to 313. The multilayered gas sensor element 1 is mounted on a clamp (not shown) at the loader section 32. The side surface grinding section 33 is provided for grinding both side surfaces of the multilayered gas sensor element 1. The multilayered gas sensor element 1 is released from the clamp at the unloader section 34 when the grinding operation of the side surfaces is accomplished. The ridge chamfering section 35 is provided for chamfering the ridge portions.

In the side surface grinding section 33, two side surface grinding disk grindstones 331 and 333 are provided for grinding the side surfaces of the multilayered gas sensor element 1. The side surface grinding grindstones 331 and 333 respectively stand perpendicularly to the horizontal direction and have disk faces opposing in parallel with each other (refer to FIG. 9). Furthermore, the side surface grinding grindstones 331 and 333 rotate about rotational shafts 332 and 334 located at their disk centers, as indicated by arrow 'a' in FIG. 6. Furthermore, the multilayered gas sensor element 1 is introduced from the side closer to the loader section 32 in the direction opposed to the arrow 'a.'

In the ridge chamfering section 35, two ridge chamfering disk grindstones 351 and 352 are provided for chamfering the ridge portions of the multilayered gas sensor element 1. The ridge chamfering disk grindstones 351 and 352, having disk faces extending in the horizontal direction, are placed adjacently. The ridge chamfering disk grindstones 351 and 352 rotate in the counterclockwise direction about rotational shafts located at their disk centers, as indicated by arrows 'b' in FIG. 6.

The operation of the above-described grinding apparatus 3 will be explained with reference to FIGS. 6 to 16.

The robot arm 311 conveys a non-processed multilayered gas sensor element 1 from a pallet 300 to the loader section 32. In the loader section 32, the multilayered gas sensor element 1 is held with the clamp (not shown).

Figure 9:
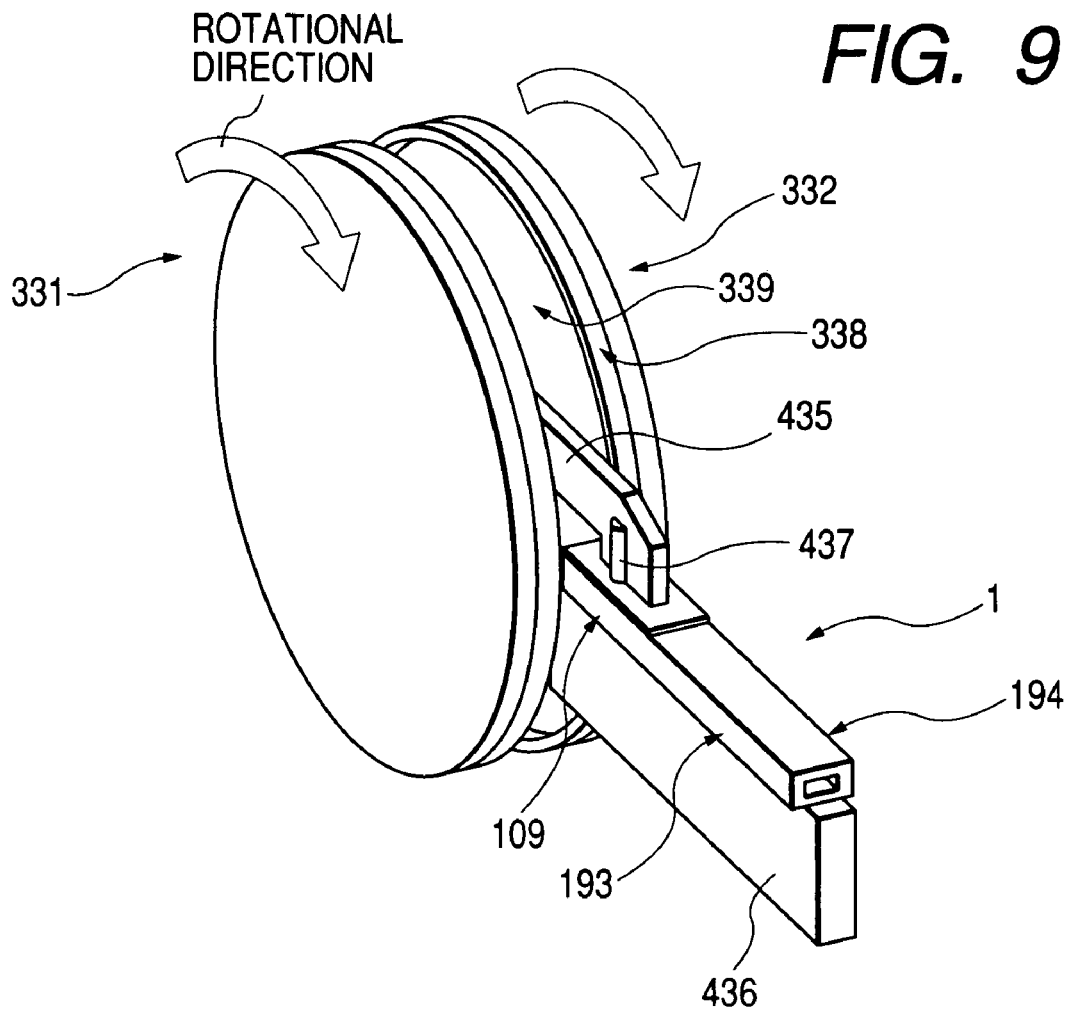
FIG. 9 is a perspective view explaining the side surface grinding operation in accordance with the preferred embodiment of the present invention.
Figure 11:
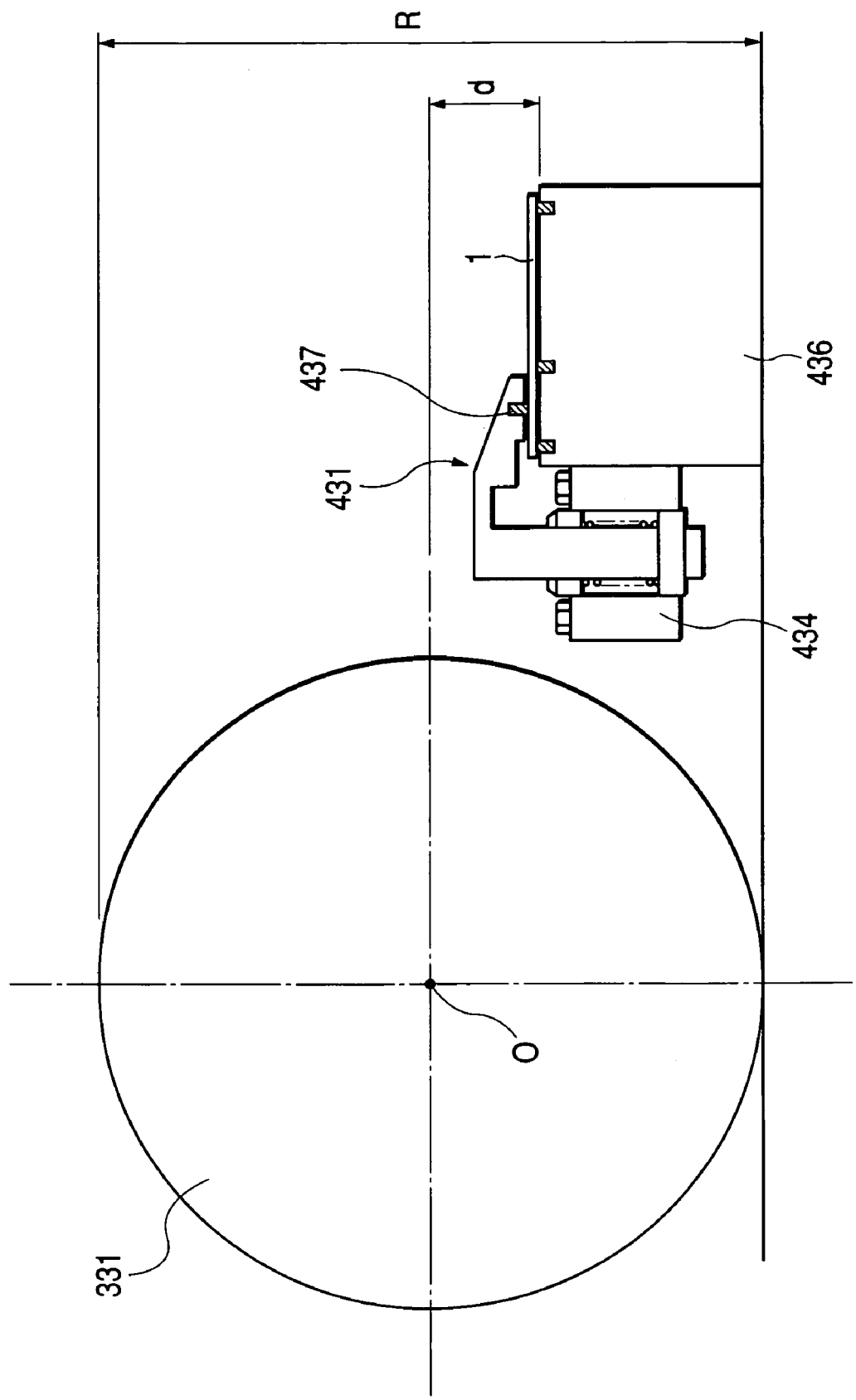
FIG. 11 is a view explaining the positional relationship between the side surface grinding disk grindstones and a multilayered gas sensor element to be introduced into a clearance of these grindstones in accordance with the preferred embodiment of the present invention.
Figure 12:
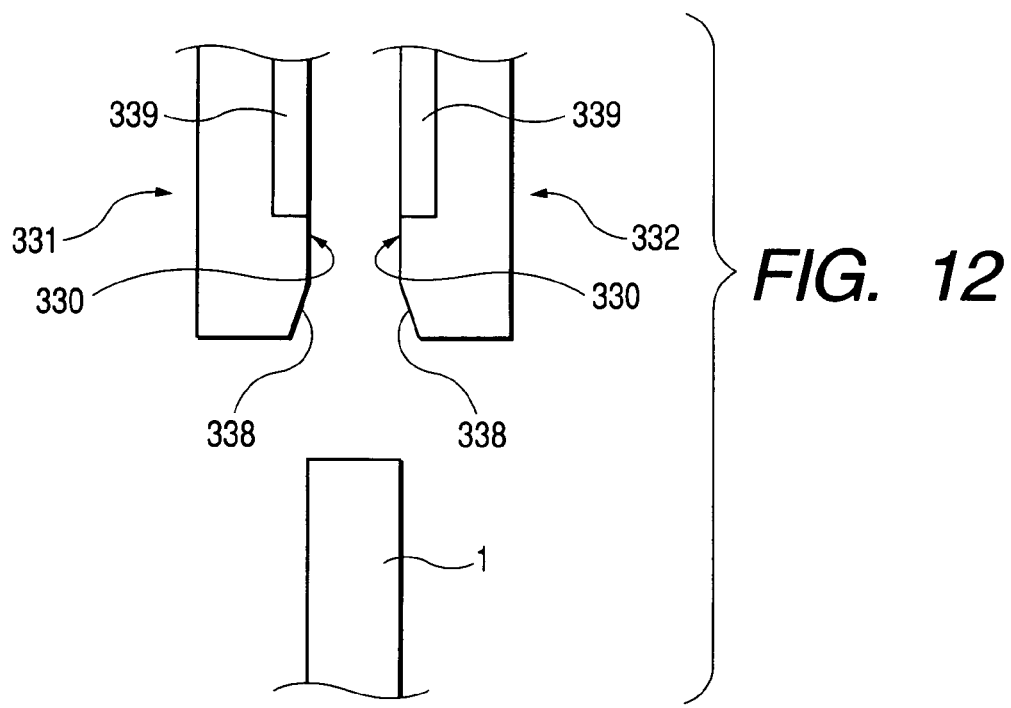
FIG. 12 is an enlarged view showing an outer circumferential region of respective side surface grinding disk grindstones in accordance with the preferred embodiment of the present invention.

Next, the multilayered gas sensor element 1 held by the above-described clamp is introduced into a clearance between two side surface grinding disk grindstones 331 and 333 positioned in the side surface grinding section 33, being led from a longitudinal front end side where the sensor cell is present (indicated by reference numeral 109 shown in FIG. 1). The grinding operation of the side surfaces of the multilayered gas sensor element 1 is carried out when the multilayered gas sensor element 1 passes the clearance between the opposed side surface grinding disk grindstones 331 and 333. In other words, the side surfaces of the multilayered gas sensor element 1 are simultaneously ground. FIG. 7 is a side view showing the side surface grinding section 33. FIGS. 9, 11 and 12 show the condition of the multilayered gas sensor element 1 held by a clamp 431 which is guided into the clearance between two side surface grinding disk grindstones 331 and 333.

Besides the clamp 431 for holding the multilayered gas sensor element 1, the side surface grinding section 33 includes an accommodation sleeve 434 and a grinding table, as shown in FIG. 7. The accommodation sleeve 434 accommodates a cylinder 433 and a proximal end portion of the clamp 431. The cylinder 433 drives the clamp 431. The side surface grinding disk grindstones 331 and 333 are placed on the grinding table. The clamp 431, as shown in FIG. 9, includes a pressing portion 435 and a support table 436 which cooperatively supports and fixes the front end portion 109 of the multilayered gas sensor element 1. A columnar rubber member 437 is attached to the bottom surface of the pressing portion 435, so that the multilayered gas sensor element 1 is directly pressed by the rubber member 437. Furthermore, two other rubber members 437 are provided on the upper surface of the support table 436 as shown in FIG. 7. In other words, the multilayered gas sensor element 1 is substantially fixed with a total of three rubber members 437.

Figure 8:
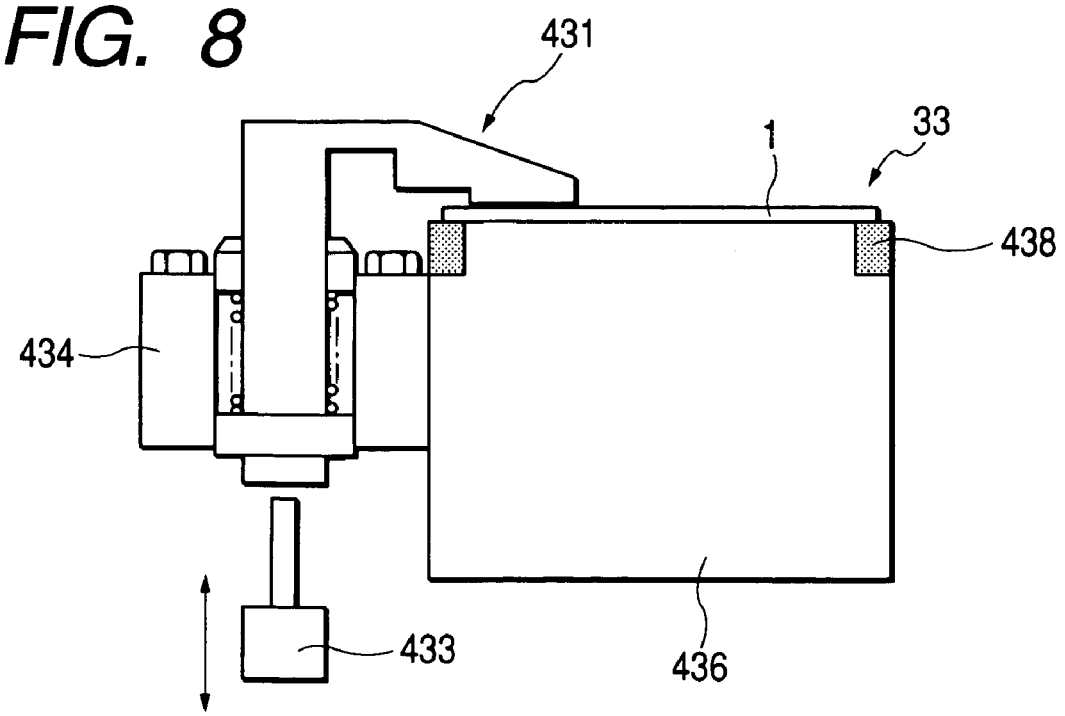
FIG. 8 is a view showing another side surface grinding section of the grinding apparatus in accordance with the preferred embodiment of the present invention.

According to this supporting structure, each rubber member 437 supports the multilayered gas sensor element 1 with a very narrow contact area which is about 3.5 mm in diameter and 9.6 mm$^2$ in area. In other words, the multilayered gas sensor element 1 is substantially supported and fixed at point. However, as shown in FIG. 8, instead of providing the rubber members 437, it is preferable that the pressing portion 435 and the support table 436 are partly made of elastic rubber materials 438 so that the multilayered gas sensor element 1 can be directly supported with rubber materials 438.

The process of introducing the multilayered gas sensor element 1 between the side surface grinding disk grindstones 331 and 332 is carried out within the region of the diameter R of respective grindstones 331 and 332 as shown in FIG. 11. The distance between the center O of respective grindstones 331 and 332 (although the grindstone 332 is omitted in FIG. 11) and the surface of the support table 436 is 55 mm (indicated by 'd' in FIG. 11). The diameter R of respective grindstones 331 and 332 is 200 mm.

Figure 13:
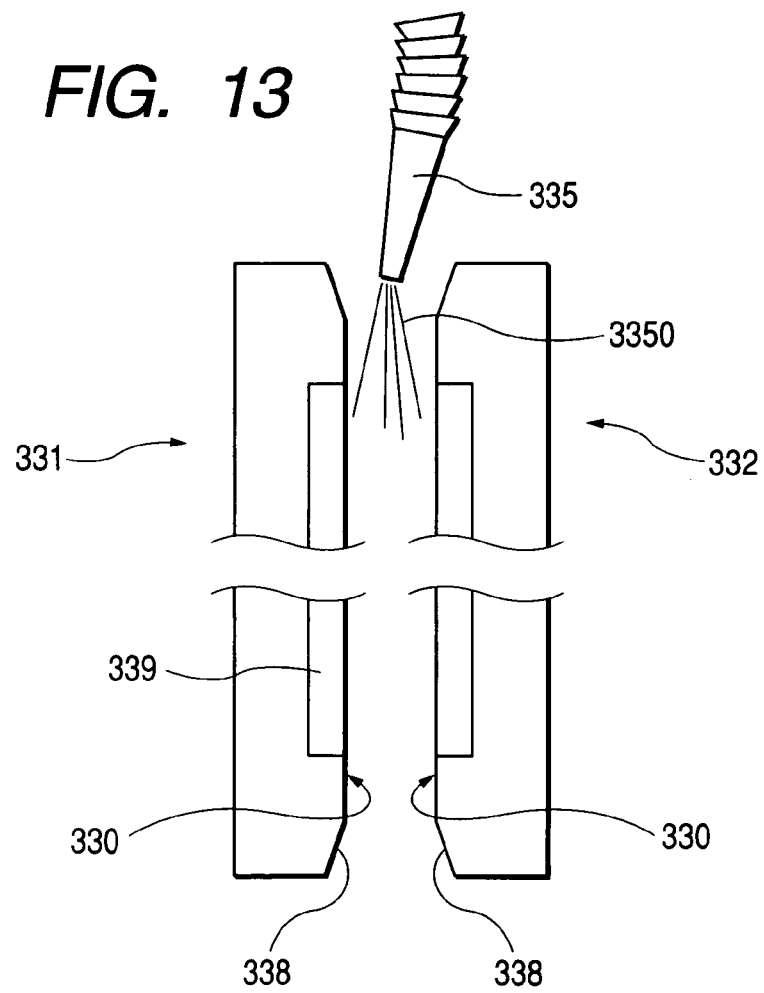
FIG. 13 is a view showing injection of grinding fluid into the clearance between two side surface grinding disk grindstones in accordance with the preferred embodiment of the present invention.

As shown in FIG. 12, each of the side surface grinding disk grindstones 331 and 332 has a tapered circumferential region 338, so that the multilayered gas sensor element 1 can be smoothly introduced. Furthermore, as shown in FIG. 13, the side surface grinding disk grindstones 331 and 332 have opposed disk faces 330 each of which is provided with a recess serving as a grinding fluid storage pocket 339. More specifically, during the grinding operation for the side surfaces of the multilayered gas sensor element 1, an injection nozzle 335 supplies grinding fluid 3350 (such as pure water) into the clearance between two side surface grinding disk grindstones 331 and 332. Providing the above-described grinding fluid storage pocket 339 is effective to temporarily store the injected grinding fluid 3350. The consumption amount of the grinding fluid 3350 can be suppressed. The manufacturing costs for the multilayered gas sensor element 1 can be reduced.

Furthermore, in the grinding operation of the side surfaces of the multilayered gas sensor element 1, the side surface grinding disk grindstones 331 and 332 rotate in the direction shown in FIG. 9, i.e., from top to bottom at the portion where the side surfaces of the multilayered gas sensor element 1 are processed. Thus, the rotating disk grindstones 331 and 332 cooperatively press the multilayered gas sensor element 1 from above, thereby realizing the downcut processing so as to prevent the multilayered gas sensor element 1 from floating from the support table 436.

Figure 10:
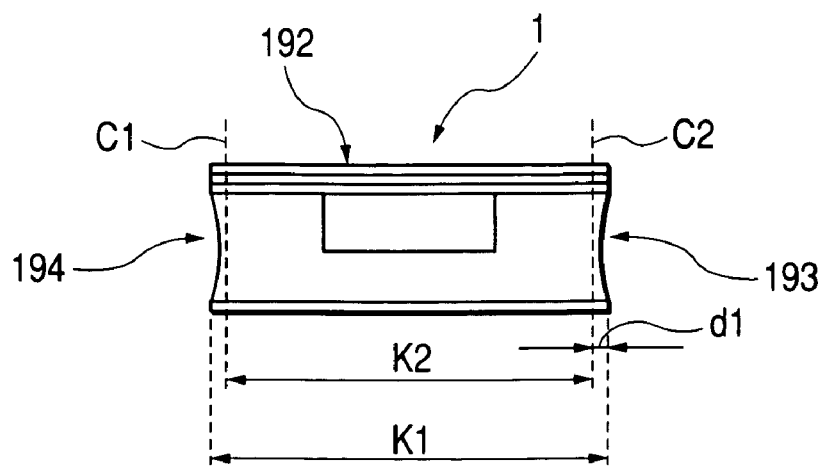
FIG. 10 is a view explaining the grinding depth in the side surface grinding operation in accordance with the preferred embodiment of the present invention.

In this side surface grinding section 33, the gas sensor element 1 is processed until the side surfaces 193 and 194 reach the dotted lines c1 and c2 shown in FIG. 10. As shown in this drawing, there is the tendency that the multilayered gas sensor element 1 has warpage on respective side surfaces 193 and 194 immediately after accomplishing the sintering operation.

Thereafter, in the unloader section 34, the robot arms 312 and 313 release the multilayered gas sensor element 1 from the clamp 431. In this condition, the multilayered gas sensor element 1 has fresh side surfaces being finished by the above-described grinding operation. The multilayered gas sensor element 1 is temporarily placed in the unloader section 34. Then, the multilayered gas sensor element 1 is conveyed to the ridge chamfering section 35.

The ridge chamfering section 35, as shown in FIGS. 14 to 19, includes a frame 452 which holds the ridge chamfering disk grindstone 351 (or 352) rotating on a support base 450, a guard 451 surrounding the ridge chamfering disk grindstone 351 (or 352) to prevent the grinding dusts and water from scattering outward during the grinding operation, and a hose 453 supplying the grinding fluid 4530 (pure water or the like) during the grinding operation.

Figure 14:
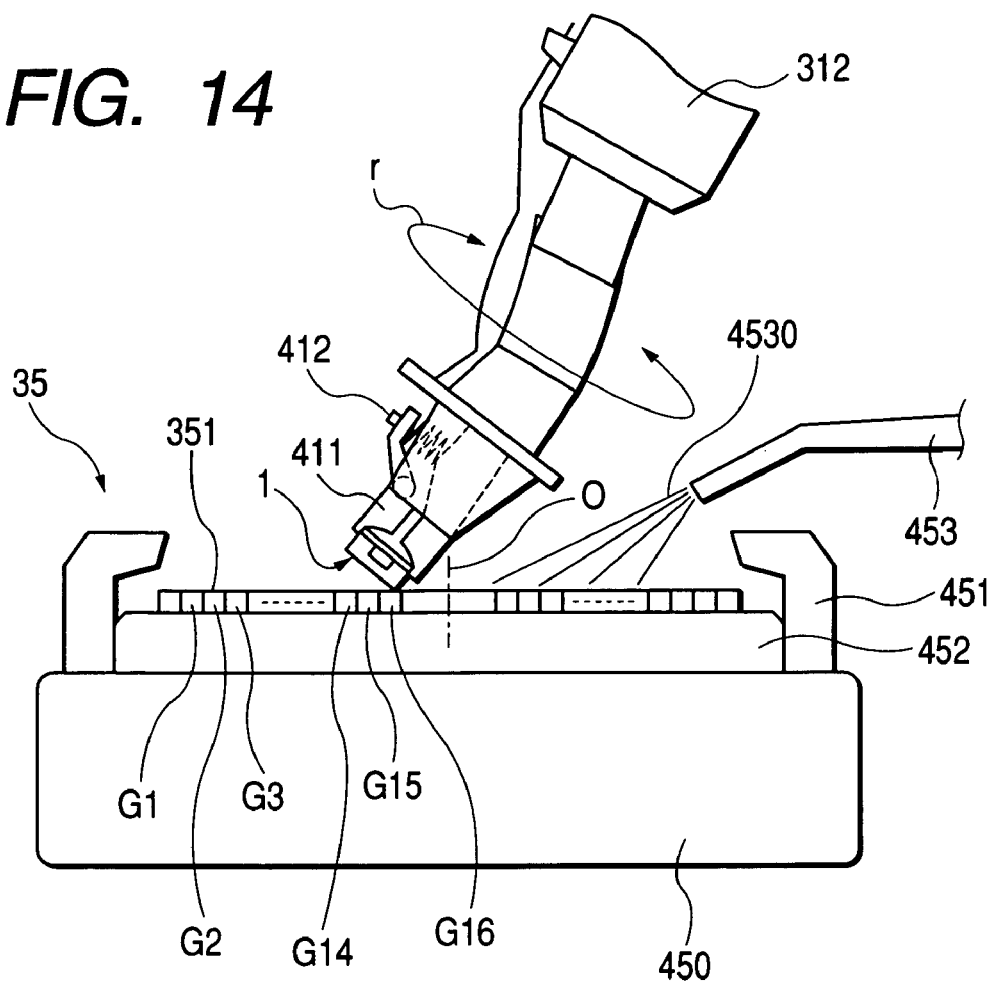
FIG. 14 is a view showing a ridge chamfering section of the grinding apparatus in accordance with the preferred embodiment of the present invention.

Then, as shown in FIG. 14, the robot arm 312 (or 313) grabs the multilayered gas sensor element 1 and transfers it to the ridge chamfering section 35. The chamfering operation is carried out under the condition that the ridge portion 196 is pressed against the ridge chamfering disk grindstone 351 (or 352) with an inclined angle of 45°, until the chamfered surface reaches a dotted line C3. This chamfering operation is performed independently for each of the ridge portions 196. Each of the robot arms 312 and 313 has a chuck 411 provided at its distal end for holding the multilayered gas sensor element 1. A chuck spring 412, associated with chuck 411, adjusts the pressure for holding the multilayered gas sensor element 1.

Figure 15:
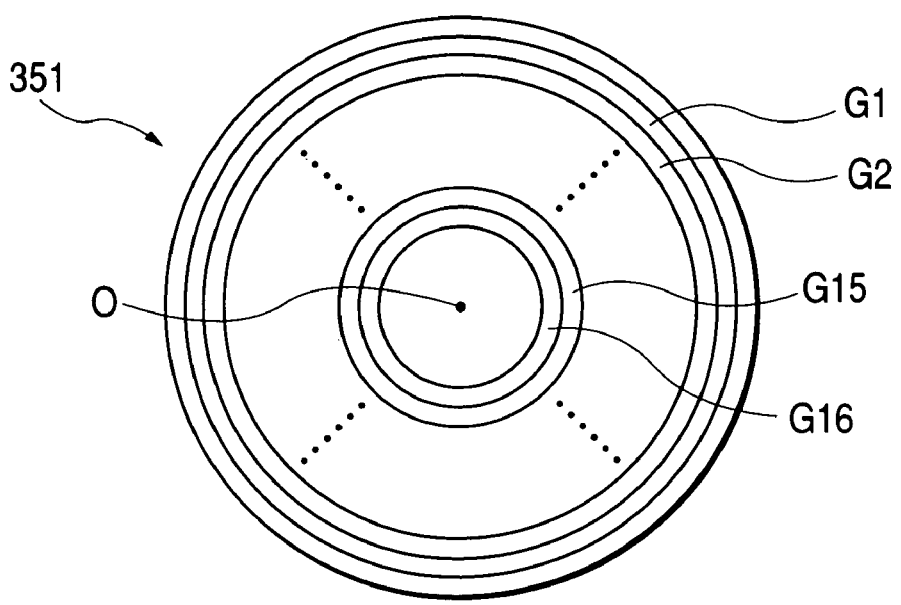
FIG. 15 is a plan view showing a ridge chamfering disk grindstone in accordance with the preferred embodiment of the present invention.

Hereinafter, the processes of the chamfering operation for the ridge portions 196 of the multilayered gas sensor element 1 will be explained in more detail. As shown in FIGS. 14 and 15, the ridge chamfering disk grindstone 351 is dissected into a total of 16 coaxial annular sectors G1, G2, - - -, G15, and G16 sequentially arranged from the outer peripheral edge to the center O. An ordinary motor is used to rotate the ridge chamfering disk grindstone 351. The ridge chamfering disk grindstone 351 works as a constant rotational speed type (i.e., a constant angular speed type). Accordingly, the innermost annular sector G16 has a slow line speed, while the outermost annular sector G1 has a high line speed. Accordingly, it is possible to grind the ridge portion 196 much by pressing it to the outermost annular sector G1 and little by pressing it to the innermost annular sector G16.

According to this embodiment, the ridge portion 196 is pressed against the outermost annular sector G1 for 3.0 seconds and is once released from the ridge chamfering disk grindstone 351. Then, the robot arm 312 (or 313) rotates in the direction indicated by an arrow 'r' in FIG. 14, so that the multilayered gas sensor element 1 is reversed in the longitudinal direction. In this condition, the other ridge portion 196 is pressed against the annular sector G2 of the disk grindstone 351 for 3.2 seconds. Thereafter, the above-described ridge chamfering operation is successively repeated by changing the sector of the ridge chamfering disk grindstone 351 in the order of G3, G4, - - -, G16, while the chamfering time increases stepwise by the increment of 0.2 second. As a result, the chamfering operation of the ridge portion 196 at the final sector G16 is performed for 6.0 seconds. By accomplishing the above-described grinding operations, the multilayered gas sensor element 1 having newly chamfered ridge portions 196 at right and left sides is obtained.

Figure 17:
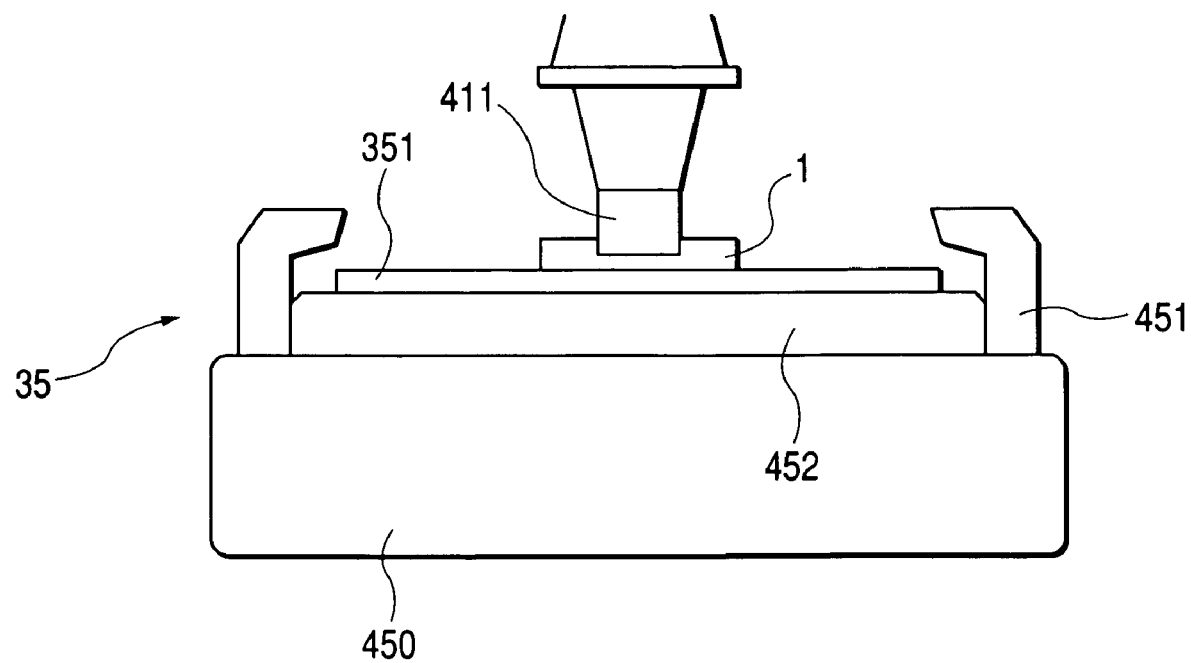
FIG. 17 is a view showing the ridge chamfering operation, seen from the side, in accordance with the preferred embodiment of the present invention.
Figure 18A:
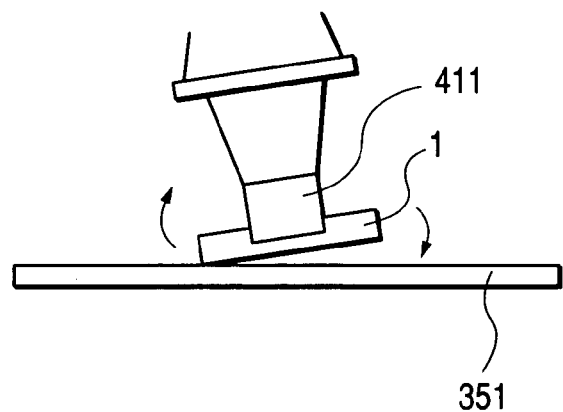
FIGS. 18A and 18B are views explaining the swing movement of the multilayered gas sensor element during the ridge chamfering operation in accordance with the preferred embodiment of the present invention.
Figure 18B:
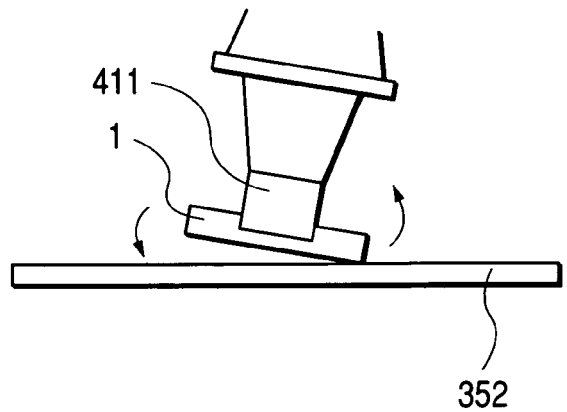
Figure 19:
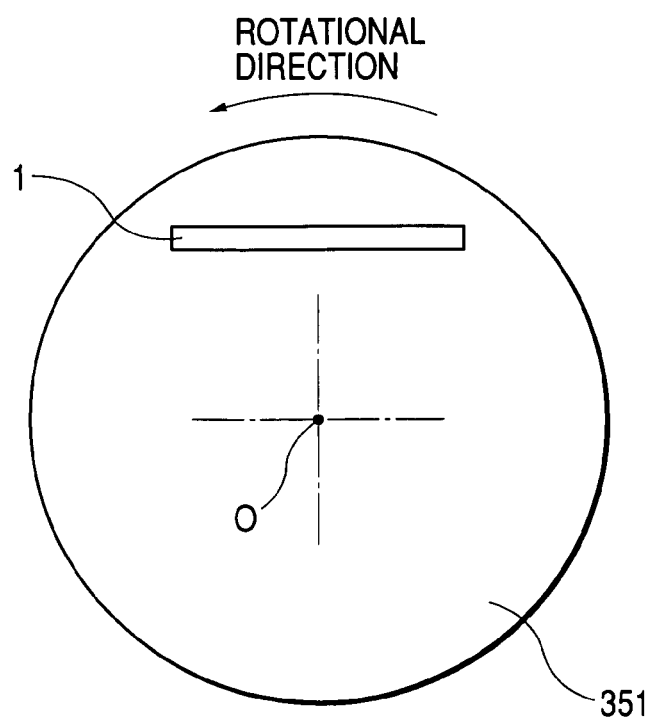
FIG. 19 is a plan view showing the ridge chamfering operation, seen from the direction perpendicular to the disk face.

FIG. 19 shows the chamfering operation of the ridge portion 196, seen from the direction perpendicular to the disk face. As shown in this drawing, the disk grindstone 351 rotates in the counterclockwise direction. The longitudinal direction of the multilayered gas sensor element 1 is positioned in parallel with this rotational direction when the ridge portion 196 is chamfered. FIG. 17 shows the chamfering operation of the ridge portion 196, seen from the direction parallel to the disk face. As shown in FIGS. 18A and 18B, the chamfering operation of the ridge portion 196 is carried out by swinging the element in the longitudinal direction.

After finishing the chamfering operation for two ridge portions, the robot arms 312 and 313 hold the multilayered gas sensor element 1 and convey it to the unloader section 34. Then, the robot arm 311 grabs the multilayered gas sensor element 1 to the original position on the pallet 300.

As a result of the grinding operation of the side surfaces 193 and 194, the average width K2 of the multilayered gas sensor element 1 becomes 4.5 mm to 4.6 mm, whereas the initial average width k1 of the multilayered gas sensor element 1 being not processed by the grinding operation is 4.8 mm, as shown in FIG. 10. The used side surface grinding disk grindstones 331 and 332 are made of diamond #500 metal and have the dimensions of 200 mm in diameter and 3.0 mm in width. The rotational speed is 3,000 RPM. The clamp load against the multilayered gas sensor element 1 is 49N. The shifting speed of the multilayered gas sensor element 1 introduced into the clearance between two side surface grinding disk grindstones 331 and 332 is 20 mm/s.

Figure 16:
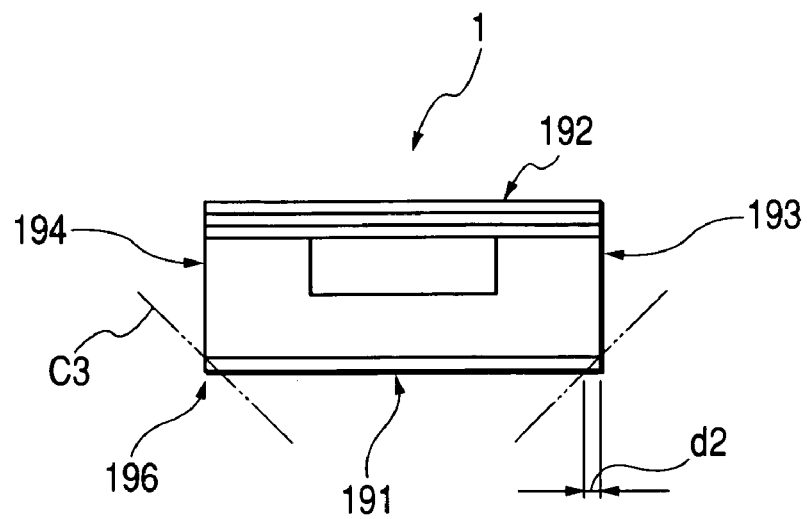
FIG. 16 is a view explaining the chamfering depth in the ridge chamfering operation in accordance with the preferred embodiment of the present invention.

In the chamfering operation of the above-described ridge portion 196, the chamfering depth d2 of the obtained chamfered surface is 0.05 mm to 0.25 mm as shown in FIG. 16. The used ridge chamfering disk grindstones 351 and 352 are made of diamond cloth #1200. The rotational speed is 360 RPM. The load for pressing the multilayered gas sensor element 1 against the ridge chamfering disk grindstones 351 and 352 is 19.8N. The pressing time, i.e., chamfering time is 3.0 to 6.0 seconds.

Furthermore, according to the above-described grinding apparatus 3 and the grinding method, it is possible to unify the time required for accomplishing the ridge grinding operation for each multilayered gas sensor element 1 by successively and repetitively pressing the multilayered gas sensor element 1 to various positions of the ridge chamfering disk grindstone 351 and 352 different in the distance from the disk center O.

Thus, it becomes possible to unify the processing time required for chamfering the ridge portions 196 of each multilayered gas sensor element 1. The processing cycle in the manufacturing of the multilayered gas sensor element becomes constant and stable. Furthermore, it becomes possible to prevent the ridge chamfering disk grindstones 351 and 352 from being locally worn out and accordingly the lifetime of respective grindstones can be extended.

Inspection

The multilayered gas sensor element, being processed by the above-described grinding and chamfering operations, is then subjected to various inspections.

More specifically, after removing the surface defects from the sensor element, the discrimination between a detective product and a non-defective product is carried out by:

(I) inspecting the processed surfaces obtained by grinding both side surfaces or obtained by chamfering the ridge portions with an image recognizing apparatus to check whether or not these surfaces satisfy predetermined size requirements;

(II) inspecting the presence of any chipping caused in the grinding or chamfering operation;

(III) visually inspecting the presence of any growth of surface defects by supplying electric power to the heater portion; and (IV) inspecting the largeness of an insulation resistance of the multilayered gas sensor element.

The above-described inspections (I) and (II) are carried out in the following manner.

An image recognizing apparatus equipped with a CCD (i.e., charge-coupled device) is used to pick up an image of reflected light under a condition that light is irradiated on the ground surface of the multilayered gas sensor element 1. In this inspection, it is checked whether or not the dimensions of each multilayered gas sensor element and resulting chipping sizes satisfy the predetermined regulations. The multilayered gas sensor element having chipping is regarded as a defective product. Sorting of finished multilayered gas sensor elements is carried out so as to exclude these defective products.

In the above-described inspections (III), as shown in FIG. 5, the heater terminals are connected to an electric power source and the direct-current voltage of 14.5V is applied to the heater terminals. The heater portion generates heat in response to supply of electric power, and a significant thermal stress acts on the multilayered gas sensor element. An inspector (or a worker) checks visually the presence of any growth of surface defects, such as breaks and cracks caused by the thermal stress, and also checks whether or not any new surface defects appear, to select only non-defective products.

In the above-described inspections (IV), the insulation resistance of each multilayered gas sensor element is measured by the following method. More specifically, the voltage of 500V is applied to the heater terminals under a condition that the multilayered gas sensor element is immersed in alcohol. If any cracks or other surface defects are present in the vicinity of the heater portion, alcohol will enter inside the element and the insulation resistance will decrease. Accordingly, the insulation properties of the multilayered gas sensor element can be evaluated by measuring the current flowing between the heater terminals and alcohol. And, therefore, non-defective products are discriminable from defective products.

Through the above-described four inspection processes, it becomes possible to selectively sort the multilayered gas sensor elements having no adverse surface defects.

Employing the above-described inspections makes it possible to improve the production yield in the manufacturing of the multilayered gas sensor elements.

The multilayered gas sensor element having a deteriorated insulation resistance will have insufficient airtightness for the reference gas chamber 150 shown in FIG. 3. The concentration of a reference gas will not be stable. Measurement of the gas concentration in the measured gas will not be accurately performed. Accordingly, such a sensor element is not reliable and cannot be used for accurate measurement. Especially, the multilayered gas sensor element is installed in an exhaust passage of an automotive engine to measure the oxygen concentration in the exhaust gas or the air-fuel ratio or $\lambda$ point of the engine required in combustion control of the engine. In such a case, the multilayered gas sensor element must be highly accurate to reduce the harmful substances causing air pollution. In this respect, the above-described manufacturing method assures the manufacturing of excellent multilayered gas sensor elements.

What is claimed is:

1. A method for manufacturing a multilayered gas sensor element which includes a sensor cell for measuring a specific gas concentration in a measured gas, a main body portion including a plurality of laminated ceramic substrates, and a plate heater portion generating heat in response to supply of electric power, which are integrally laminated in a predetermined order, comprising the steps of:

sintering a multilayered body of green sheets forming said main body portion and said heater portion into a multilayered gas sensor element; and grinding at least both side surfaces of said multilayered gas sensor element extending in a longitudinal direction, thereby removing surface defects, wherein two side surface grinding disk grindstones, each rotating about its disk center, are disposed in parallel with each other to grind said both side surfaces of said multilayered gas sensor element extending in the longitudinal direction, and said multilayered gas sensor element is introduced into a clearance between said two side surface grinding disk grindstones to grind said both side surfaces, wherein an upper surface of said multilayered gas sensor element is substantially supported at a point when said multilayered gas sensor element is introduced into the clearance between said two side surface grinding disk grindstones to grind the side surfaces of said multilayered gas sensor element, and wherein after removing said surface defects from the sensor element, discrimination between a detective product and a non-defective product is carried out by:

inspecting the processed surfaces obtained by grinding said both side surfaces with an image recognizing apparatus to check whether or not these surfaces satisfy predetermined size requirements;

inspecting the presence of any chipping caused in the grinding operation;

visually inspecting the presence of any growth of surface defects by supplying electric power to said heater portion; and inspecting the largeness of an insulation resistance of said multilayered gas sensor element.

2. The manufacturing method for a multilayered gas sensor element in accordance with claim 1, wherein a holder is used to support and fix said multilayered gas sensor element when said multilayered gas sensor element is introduced into the clearance between said two side surface grinding disk grindstones to grind the side surfaces of said multilayered gas sensor element, and a portion of said holder being directly brought into contact with said multilayered gas sensor element is made of an elastic member.

3. The manufacturing method for a multilayered gas sensor element in accordance with claim 1, wherein said multilayered gas sensor element is introduced into the clearance between said two side surface grinding disk grindstones to grind the side surfaces of said multilayered gas sensor element, being led from a longitudinal front end side where said sensor cell is present.

4. A method for manufacturing a multilayered gas sensor element which includes a sensor cell for measuring a specific gas concentration in a measured gas, a main body portion including a plurality of laminated ceramic substrates, and a plate heater portion generating heat in response to supply of electric power, which are integrally laminated in a predetermined order, comprising the steps of:

sintering a multilayered body of green sheets forming said main body portion and said heater portion into a multilayered gas sensor element; and grinding at least both side surfaces of said multilayered gas sensor element extending in a longitudinal direction, thereby removing surface defects, wherein after removing said surface defects from the sensor element, discrimination between a detective product and a non-defective product is carried out by:

inspecting the processed surfaces obtained by grinding said both side surfaces with an image recognizing apparatus to check whether or not these surfaces satisfy predetermined size requirements;

inspecting the presence of any chipping caused in the grinding operation;

visually inspecting the presence of any growth of surface defects by supplying electric power to said heater portion; and inspecting the largeness of an insulation resistance of said multilayered gas sensor element.

5. The manufacturing method for a multilayered gas sensor element in accordance with claim 4, wherein two side surface grinding disk grindstones, each rotating about its disk center, are disposed in parallel with each other to grind said both side surfaces of said multilayered gas sensor element extending in the longitudinal direction, and said multilayered gas sensor element is introduced into a clearance between said two side surface grinding disk grindstones to grind said both side surfaces.

6. The manufacturing method for a multilayered gas sensor element in accordance with claim 5, wherein said multilayered gas sensor element is substantially supported and fixed at point when said multilayered gas sensor element is introduced into the clearance between said two side surface grinding disk grindstones to grind the side surfaces of said multilayered gas sensor element.

7. The manufacturing method for a multilayered gas sensor element in accordance with claim 5, wherein a holder is used to support and fix said multilayered gas sensor element when said multilayered gas sensor element is introduced into the clearance between said two side surface grinding disk grindstones to grind the side surfaces of said multilayered gas sensor element, and a portion of said holder being directly brought into contact with said multilayered gas sensor element is made of an elastic member.

8. The manufacturing method for a multilayered gas sensor element in accordance with claim 5, wherein said multilayered gas sensor element is introduced into the clearance between said two side surface grinding disk grindstones to grind the side surfaces of said multilayered gas sensor element, being led from a longitudinal front end side where said sensor cell is present.

* * * * *